US010945515B2

(12) United States Patent
Meschkat et al.

(10) Patent No.: US 10,945,515 B2
(45) Date of Patent: Mar. 16, 2021

(54) PERSONAL CARE DEVICE WITH AUDIBLE FEEDBACK

(71) Applicant: The Procter & Gamble Company, Cincinnati, OH (US)

(72) Inventors: Stephan James Andreas Meschkat, Bad Soden (DE); Thomas Elliot Rabe, Baltimore, MD (US); Rebecca Ashley Kolakoski, Cincinnati, OH (US); Brian Lee Floyd, Cincinnati, OH (US); Faiz Feisal Sherman, Mason, OH (US); Paul Vernon, Mason, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 257 days.

(21) Appl. No.: 16/006,944

(22) Filed: Jun. 13, 2018

(65) Prior Publication Data

US 2018/0360196 A1  Dec. 20, 2018

Related U.S. Application Data

(60) Provisional application No. 62/520,966, filed on Jun. 16, 2017.

(51) Int. Cl.
*A61M 11/00* (2006.01)
*A45D 44/00* (2006.01)
(Continued)

(52) U.S. Cl.
CPC .......... *A45D 44/005* (2013.01); *A45D 19/00* (2013.01); *A61B 5/0036* (2018.08);
(Continued)

(58) Field of Classification Search
None
See application file for complete search history.

(56) References Cited

U.S. PATENT DOCUMENTS 4,129,391 A    12/1978  Gamacher
4,270,526 A     6/1981  Morales
(Continued)

FOREIGN PATENT DOCUMENTS

AU   2014200087 A1   1/2014
CN     107521229 B   5/2019
(Continued)

OTHER PUBLICATIONS

International Search Report and Written Opinion for PCT/US2018/037227 dated Jun. 13, 2018.
(Continued)

*Primary Examiner* — Brent Swarthout
(74) *Attorney, Agent, or Firm* — Melissa G Krasovec; Amanda Marie Herman

(57) ABSTRACT

A personal care device for modifying a keratinous surface having a sensor, a treatment element adapted to deposit a personal care composition, a feedback element, and a processor. The feedback element can be activated during deposition of the personal care composition. The personal care device can analyze a keratinous surface, identify keratinous imperfections, and then modify the keratinous imperfection by depositing a personal care composition. The feedback element can be intermittently activated during deposition and can emit a feedback signal that corresponds to the deposition of the personal care composition to alert the user as to how the personal care device is working and/or when the modification process is complete.

15 Claims, 4 Drawing Sheets

(51) Int. Cl.
    *A45D 19/00*       (2006.01)
    *G06T 7/00*        (2017.01)
    *A61B 5/00*        (2006.01)
    *B41J 3/407*       (2006.01)
    *A45D 19/16*       (2006.01)
    *A45D 33/02*       (2006.01)
    *A45D 40/26*       (2006.01)

(52) U.S. Cl.
    CPC .......... *A61B 5/0037* (2013.01); *A61B 5/0077*
        (2013.01); *A61B 5/444* (2013.01); *A61B 5/445*
        (2013.01); *A61B 5/4839* (2013.01); *A61B*
        *5/7415* (2013.01); *B41J 3/407* (2013.01);
        *G06T 7/0012* (2013.01); *A45D 19/0066*
        (2021.01); *A45D 19/16* (2013.01); *A45D 33/02*
        (2013.01); *A45D 40/26* (2013.01); *A45D*
        *2044/007* (2013.01); *A45D 2200/054*
        (2013.01); *A45D 2200/10* (2013.01); *A45D*
        *2200/1072* (2013.01); *G06T 2207/30088*
        (2013.01)

(56) References Cited

U.S. PATENT DOCUMENTS

| | | | |
|---|---|---|---|
| 4,813,404 | A | 3/1989 | Vallis |
| 5,706,038 | A | 1/1998 | Jackson |
| 6,017,110 | A | 1/2000 | Jackson |
| 6,290,324 | B1 | 9/2001 | Jackson |
| 6,312,124 | B1 | 11/2001 | Desormeaux |
| 6,622,733 | B2 | 9/2003 | Saksa |
| 6,723,077 | B2 | 4/2004 | Pickup |
| 6,810,130 | B1 | 10/2004 | Aubert |
| 7,500,732 | B2 | 3/2009 | James |
| 7,544,190 | B2 | 6/2009 | Pickup |
| 7,648,364 | B2 | 1/2010 | Dauga |
| 7,798,599 | B2 | 9/2010 | Michael |
| 7,824,003 | B2 | 11/2010 | Studer |
| 7,890,152 | B2 | 2/2011 | Edgar |
| 8,007,062 | B2 | 8/2011 | Edgar |
| 8,027,505 | B2 | 9/2011 | Edgar |
| 8,231,292 | B2 | 7/2012 | Rabe |
| 8,695,610 | B2 | 4/2014 | Samain |
| 8,915,562 | B2 | 12/2014 | Edgar |
| 8,942,775 | B2 | 1/2015 | Edgar |
| 9,020,184 | B2 | 4/2015 | Edgar |
| 9,084,587 | B2 | 7/2015 | Eckhouse |
| 9,247,802 | B2 | 2/2016 | Edgar |
| 9,271,554 | B2 | 3/2016 | Nakashima |
| 9,449,382 | B2 | 9/2016 | Edgar |
| 9,462,872 | B2 | 10/2016 | Edgar |
| 9,522,101 | B2 | 12/2016 | Rabe |
| 9,592,666 | B2 | 3/2017 | Bush |
| 9,616,447 | B2 | 4/2017 | Bush |
| 9,616,668 | B1 | 4/2017 | Rabe |
| 9,616,692 | B1 | 4/2017 | Rabe |
| 9,650,525 | B1 | 5/2017 | Suthar |
| 9,757,947 | B2 | 9/2017 | Kuno |
| 9,782,971 | B2 | 10/2017 | Vernon |
| 9,814,904 | B2 | 11/2017 | Jones |
| 9,878,554 | B1 | 1/2018 | Komplin |
| 9,907,734 | B2 | 3/2018 | Rabe |
| 9,924,875 | B2 | 3/2018 | Rabe |
| 9,925,362 | B2 | 3/2018 | Rabe |
| 9,928,591 | B2 | 3/2018 | Rabe |
| 9,949,547 | B2 | 4/2018 | Rabe |
| 9,949,552 | B2 | 4/2018 | Rabe |
| 9,955,769 | B2 | 5/2018 | Rabe |
| 9,962,532 | B2 | 5/2018 | Rabe |
| 10,016,046 | B2 | 7/2018 | Edgar |
| 10,035,355 | B2 | 7/2018 | Komplin |
| 10,043,292 | B2 | 8/2018 | Edgar |
| 10,092,082 | B2 | 10/2018 | Edgar |
| 10,117,500 | B2 | 11/2018 | Samain |
| 10,163,230 | B2 | 12/2018 | Edgar |
| 10,166,799 | B2 | 1/2019 | Rabe |
| 10,188,192 | B2 | 1/2019 | Rabe |
| 10,188,193 | B2 | 1/2019 | Rabe |
| 10,238,582 | B2 | 3/2019 | Rabe |
| 10,265,260 | B2 | 4/2019 | Giron |
| 10,314,378 | B2 | 6/2019 | Rabe |
| 10,391,042 | B2 | 8/2019 | Lingoes |
| 10,449,773 | B2 | 10/2019 | Komplin |
| 10,467,779 | B2 | 11/2019 | Edgar |
| 10,486,174 | B2 | 11/2019 | Edgar |
| 10,511,777 | B2 | 12/2019 | Nichols |
| 10,553,006 | B2 | 2/2020 | Iglehart |
| 10,576,746 | B2 | 3/2020 | Higuchi |
| 10,610,471 | B2 | 4/2020 | Lingoes et al. |
| 10,716,873 | B2 | 7/2020 | Bush |
| 10,813,857 | B2 | 10/2020 | Lingoes |
| 10,849,843 | B2 | 12/2020 | Lingoes |
| 2002/0155069 | A1 | 10/2002 | Pruche |
| 2003/0060810 | A1 | 3/2003 | Syrowicz |
| 2004/0073186 | A1 | 4/2004 | Cameron |
| 2004/0186373 | A1 | 9/2004 | Dunfield |
| 2004/0223985 | A1 | 11/2004 | Dunfield |
| 2005/0053628 | A1 | 3/2005 | Montanari |
| 2006/0077405 | A1 | 4/2006 | Topfer et al. |
| 2007/0889298 | | 2/2008 | Sugita et al. |
| 2007/0889292 | | 3/2008 | Omura Mitsuhiro |
| 2008/0069620 | A1 | 3/2008 | Anderson |
| 2007/0944528 | | 6/2008 | Obita et al. |
| 2008/0194971 | A1 | 8/2008 | Edgar |
| 2010/0224209 | A1 | 9/2010 | Rabe |
| 2011/0129283 | A1 | 6/2011 | Samain |
| 2011/0159463 | A1 | 6/2011 | Samain |
| 2011/0229247 | A1 | 9/2011 | Song |
| 2013/0302078 | A1* | 11/2013 | Edgar .................... A61B 5/441 401/5 |
| 2015/0196109 | A1 | 7/2015 | Edgar et al. |
| 2016/0022972 | A1 | 1/2016 | Rabe |
| 2016/0360858 | A1 | 12/2016 | Rabe |
| 2017/0157963 | A1 | 6/2017 | Rabe |
| 2017/0256084 | A1* | 9/2017 | Iglehart .............. G06K 9/00221 |
| 2018/0001646 | A1 | 1/2018 | Vernon |
| 2018/0279843 | A1 | 10/2018 | Paul |
| 2018/0310693 | A1 | 11/2018 | Edgar |
| 2018/0360190 | A1 | 12/2018 | Villalobos Lingoes |
| 2018/0360709 | A1 | 12/2018 | Rabe |
| 2018/0368727 | A1 | 12/2018 | Heath |
| 2019/0080451 | A1 | 3/2019 | Iglehart |
| 2019/0193443 | A1 | 6/2019 | Wong |
| 2019/0209425 | A1 | 7/2019 | Lee |
| 2019/0263127 | A1 | 8/2019 | Tanioku |
| 2020/0188250 | A1 | 6/2020 | Lingoes |
| 2020/0306407 | A1 | 10/2020 | Bush |
| 2020/0405602 | A1 | 12/2020 | Lingoes |

FOREIGN PATENT DOCUMENTS

| | | |
|---|---|---|
| CN | 107639939 B | 2/2020 |
| DE | 10153249 A1 | 5/2003 |
| DE | 202004003148 U1 | 3/2005 |
| ES | 2452530 T3 | 4/2014 |
| FR | 2933585 B1 | 10/2011 |
| JP | 2003052642 A | 2/2003 |
| JP | 2006271654 A | 10/2006 |
| JP | 2006297691 A | 11/2006 |
| WO | WO2006092604 A2 | 9/2006 |
| WO | 2008010628 A1 | 1/2008 |
| WO | 2008098234 A3 | 11/2008 |
| WO | 2009036876 A1 | 3/2009 |
| WO | 2009036924 A8 | 7/2009 |
| WO | 2009036925 A8 | 7/2009 |
| WO | 2010004528 A1 | 1/2010 |
| WO | 2010004531 A1 | 1/2010 |
| WO | 2010077703 A1 | 7/2010 |
| WO | 2011067761 A1 | 6/2011 |
| WO | WO2011078903 A1 | 6/2011 |
| WO | 2012103048 A3 | 10/2012 |
| WO | WO2015191821 A2 | 12/2015 |
| WO | WO2015191824 A2 | 12/2015 |

(56) References Cited

FOREIGN PATENT DOCUMENTS

| WO | WO2016014886 A1 | 1/2016 |
|----|-----------------|--------|
| WO | 2018088594 A1 | 5/2018 |
| WO | 2018185773 A1 | 10/2018 |

OTHER PUBLICATIONS

International Search Report and Written Opinion for PCT/US2018/037230 dated Aug. 22, 2018.
International Search Report and Written Opinion for PCT/US2018/037511 dated Aug. 22, 2018.
All Office Actions for U.S. Appl. No. 16/006,920, filed Jun. 13, 2018—See Private Pair.
All Office Actions for U.S. Appl. No. 16/006,970, filed Jun. 13, 2018—See Private Pair.
U.S. Appl. No. 16/006,920, filed Jun. 13, 2018, Lingoes et al.
U.S. Appl. No. 16/006,970, filed Jun. 13, 2018, Rabe et al.
U.S. Appl. No. 16/798,559, filed Feb. 24, 2020, to Janette Villalobos Lingoes et. al.
U.S. Appl. No 16/869,586, filed May 7, 2020, to Thomas Elliot Rabe et. al.
U.S. Appl. No. 17/079,547, filed Oct. 26, 2020, to Janette Villalobos Lingoes et. al.

* cited by examiner

US 10,945,515 B2

PERSONAL CARE DEVICE WITH AUDIBLE FEEDBACK

FIELD OF THE INVENTION

The present application relates generally to a personal care device for modifying a keratinous surface, and more particularly a personal care device that deposits a personal care composition onto a keratinous surface and provides audible feedback that correlates to the deposition process.

BACKGROUND OF THE INVENTION

Handheld beauty devices are becoming increasingly popular for a wide range of benefits. Hair straightening and curling devices, air brush makeup devices, light emitting diode (LED) skin care devices, mechanical cleansing brushes, and most recently, inkjet deposition devices are a few of the offerings that consumers are adopting in place of techniques which were previously manual hand applications. One of the challenges that consumers often have with adopting these new devices is the lack of visible or tactile cues to know if the device is working as intended. Another challenge that consumers frequently have with these devices is how to use the device in its best possible manner. How fast to move the device, how long to use the device, and/or how much pressure to apply when using the device are examples of the challenges that consumers can face when using a new product or device.

In one example, a consumer that is accustomed to applying skin care and/or cosmetic products with their fingers, a brush, or a sponge can see and feel the product and know how much to apply to get the desired benefit. However, if these products are applied with a micro-deposition device, like an inkjet deposition device, that is both silent in operation and deposits so little product that it is difficult to see and feel, the consumer may have difficulty knowing when and how long to apply the product or when they should move to a different part of their body. In another example, LED light therapy devices are replacing some products that were typically in the form of creams and lotions and, like micro-deposition devices, they are silent and may not leave a visible trace on the skin. As such, they also face similar challenges in optimal consumer usage.

Therefore, there is a need for a personal care device that correlates the activity of the device to a variable feedback signal.

SUMMARY OF THE INVENTION

A personal care device for modifying a keratinous surface is provided comprising (a) a sensor; (b) a treatment element adapted to deposit a personal care composition; (c) a feedback element; and (d) a processor; wherein the sensor is operatively associated with the processor; wherein the processor is operatively associated with the treatment element and the feedback element; wherein the feedback element is activated during deposition of the personal care composition.

A personal care device for modifying a keratinous surface is provided comprising (a) a sensor; wherein the sensor is a camera; (b) a treatment element comprising one or more nozzles and a cartridge containing a personal care composition; (c) a feedback element; and (d) a processor; wherein the feedback element is activated during deposition of the personal care composition; wherein the feedback element emits a feedback signal when activated and the feedback signal corresponds to the rate of deposition of the personal care composition.

A method of modifying a keratinous surface comprising the steps of (a) identifying an area of keratinous surface comprising a keratinous imperfection; (b) providing a personal care device comprising a sensor, a feedback element, and a personal care composition; (c) contacting a portion of the personal care device with the area of keratinous surface and moving the personal care device over the area of keratinous surface; (d) taking an image of the keratinous surface adjacent to the one or more nozzles; (e) identifying the keratinous imperfection; (f) depositing the personal care composition onto the keratinous imperfection; (g) intermittently providing a feedback signal to alert the user that the personal care composition is deposited.

BRIEF DESCRIPTION OF THE DRAWINGS

While the specification concludes with claims particularly pointing out and distinctly claiming the present invention, it is believed the same will be better understood from the following description taken in conjunction with the accompanying drawings in which:

DETAILED DESCRIPTION

Figure 1:
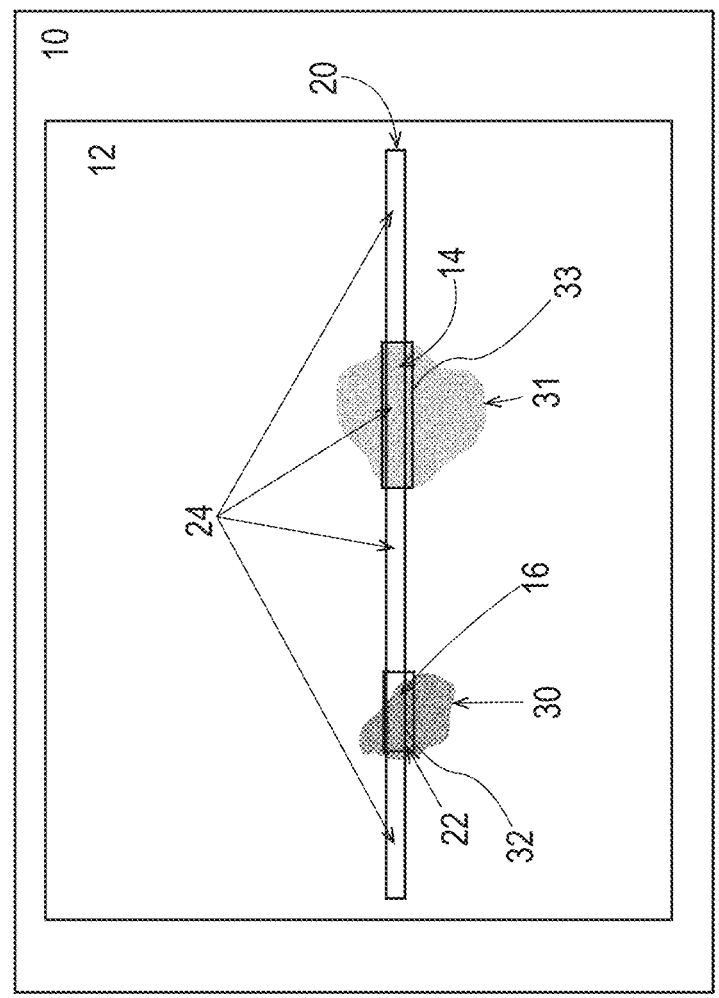
FIG. 1 is a schematic representation of an analytical window wherein a keratinous surface is analyzed by a personal care device of the present invention.

As used herein, the term "keratinous imperfection" refers to regions of skin or hair that have tonal and/or textural non-uniformities. A few non-limiting examples of the causes of such imperfection can include hyperpigmentation, skin inflammation, scarring, visible capillaries, enlarged or blocked pores, fine lines, and wrinkles.

As used herein, the term "rate of deposition" refers to the volume of the treatment composition that is deposited per unit of time.

As used herein, the articles "a" and "an" are understood to mean one or more of the material that is claimed or described.

All weights, measurements and concentrations herein are measured at 23° C. and 50% relative humidity (RH), unless otherwise specified.

All percentages, parts and ratios as used herein are by weight of the total composition, unless otherwise specified. All such weights as they pertain to listed ingredients are based on the active level and, therefore do not include solvents or by-products that may be included in commercially available materials, unless otherwise specified.

The present invention relates to a personal care device for modifying a human keratinous surface that can apply a composition(s) to the keratinous surface and which emits a feedback signal, such as an auditory signal, that is correlated to activity of the device, in particular the deposition activity of the device. In one aspect, the keratinous surface can be skin, alternatively the keratinous surface can be hair.

In one aspect, modifying a keratinous surface can mean camouflaging a keratinous imperfection by depositing a personal care composition onto the surface such that the keratinous imperfection is substantially macroscopically invisible to the naked eye. In one aspect, modifying a keratinous surface excludes laser hair removal.

The personal care device can detect a keratinous imperfection and deposit a micro-dosed amount of a personal care composition substantially only onto the keratinous imperfection and can emit a feedback signal which can be correlated to the rate of deposition of the personal care composition. This can alert the user as to how the personal care device is working, for example, when the personal care composition is being deposited, the amount of personal care composition that is being deposited, the frequency of deposition and/or when the keratinous imperfections are covered and the modification process is complete.

In one aspect, a user can modify a keratinous surface by placing a portion of the personal care device in contact with her skin and moving the personal care device across the surface of the skin. The personal care device can analyze and identify a keratinous imperfection and then deposit a personal care composition substantially only onto the identified keratinous imperfection. A feedback element within the personal care device can emit a feedback signal, such as a beep, click, vibration, musical wave file, and/or light, during deposition to alert the user that the personal care composition is being deposited.

In one aspect, the personal care device can be moved over the keratinous surface at a stroke rate of about 0.5 to about 1.5 inches per second.

In one aspect, at the beginning of the modification process many keratinous imperfections may be identified by the personal care device and the feedback element will emit more beeps because more droplets of personal care composition are being deposited. As the modification process continues and less keratinous imperfections are identified (because they have already been modified), the feedback element will emit fewer beeps because less droplets of the personal care composition are being deposited. The frequency, or rate at which the beeps occur, can decrease as fewer keratinous imperfections are modified, which can alert the user that the modification process is nearing completion. One advantage to this is that although users may not be able see the deposition of the personal care composition with the naked eye, they can know when the modification process is nearing completion and/or is complete because the feedback element will emit fewer feedback signals, alternatively it will no longer emit a feedback signal, alternatively it will emit a different feedback signal. This can help with proper usage of the personal care device.

In one aspect, the personal care device can be moved across the keratinous surface until a feedback signal is emitted at a rate of less than about 5 signals per inch, alternatively less than about 3 signals per inch, alternatively less than about 2 signals per inch. In one aspect, the personal care device can be moved across the keratinous surface until the feedback element no longer emits a feedback signal, alerting the user that keratinous imperfections are no longer detected and the modification process is complete.

In one aspect, the modification process can be complete when substantially all of the keratinous imperfections in a desired area are modified, alternatively when about 90% of keratinous imperfections are modified, alternatively about 80%, alternatively about 70%, alternatively about 60%, alternatively about 50%.

In one aspect, the personal care device can comprise a treatment element. The treatment element may be the portion of the personal care device that comprises a means for depositing a personal care composition onto a keratinous surface. Preferably, the treatment element can comprise one or nozzles and a cartridge for containing a personal care composition, which can be a skin care composition. The personal care device can comprise a sensor and a processor. The sensor can take a reading of a portion of the keratinous surface. The sensor readings can contain values selected from the group consisting of color, brightness, reflectance, refractance, temperature, texture, and combinations thereof.

In one aspect, the sensor can take at least one image of at least 10 µm$^2$ of keratinous surface and the processor can analyze the image to calculate the average background lightness (L) value of the image on a grey scale. Further, from the same image, a local L value can be calculated for individual pixels or a group of pixels. The local L value can then be compared to the background L value to identify a keratinous imperfection. A keratinous imperfection is an area of keratin where the absolute value of the difference between a local L value and the background L, (this difference being defined as "$\Delta L_M$" or the measured $\Delta L$, "$\Delta$" is commonly defined as the symbol for a difference between two values) is greater than a predetermined $\Delta L_S$ (wherein the "S" refers to a set $\Delta L$). The background L can be preset, or calculated by a variety of methods described below. The keratinous imperfection can then be modified with a personal care composition having a predetermined or variable contrast ratio. The personal care device can further comprise a feedback element that can be activated during deposition of the personal care composition by the treatment element. In one aspect, the personal care composition can be deposited with an accompanying feedback signal generated by the feedback element.

Referring now to FIG. 1, where analytical window 10 is an area that comprises a sample of keratinous surface 12 and nozzle array 20. The analytical window can be any shape including circular, square, rectangular, triangular, a parallelogram, or a polygon. Nozzle array 20 can contain individual nozzles 24 that are off, or not firing, and individual nozzles 22 that are firing. Keratinous imperfection 30 is shown underneath nozzle array section 32 and keratinous region 31 is shown underneath nozzle array section 33. Background L is calculated on and around keratinous surface 12, keratinous area 14 is where local $L_1$ is measured, and keratinous area 16 is where local $L_2$ is measured. Keratinous area 14 is under nozzle array 20 but not within a keratinous imperfection. Thus, the absolute value of local $L_1$–background L ($\Delta L_{1M}$) is less than the preset threshold to initiate nozzle firing. The $\Delta L_S$ threshold required to initiate nozzle firing is a variable and is dependent on the scale used. For example, in a case where the 0-255 gray scale is utilized then the $\Delta L_S$ threshold required to initiate nozzle firing would commonly be a value of 2 or greater. Thus, in the example shown in FIG. 1, the value of $\Delta L_{1M}$ is less than 2. Keratinous area 16 is within keratinous imperfection 30, and the absolute value of local $L_2$–background L ($\Delta L_{2M}$) is greater than about 2. Thus, the nozzles around keratinous area 14 are generally off, and the nozzles around keratinous area 16 are generally firing.

To insure the nozzles do not clog with particles or dried personal care composition, any nozzle can be fired at any time simply to keep it clean or clear, i.e., not blocked, and "healthy". The number of nozzles directly over a keratinous imperfection that are fired in response to the keratinous imperfection can be adjusted based on the size of $\Delta L_S$, the size (e.g., surface area) of the keratinous imperfection, or other parameters devised by those skilled in the art.

Modification times will vary based on the size of the keratinous surface area that needs modification and the precision and amount of the modification. For example, a woman may wish to simply touch up a few small areas on her face before going to the grocery store. This modification might take a few minutes. Alternatively, a bride might wear her wedding dress to a salon where a salon professional meticulously treats all exposed areas of skin prior to the wedding and the taking of her wedding pictures. This full body modification might take hours. Accordingly, the user will have tremendous control over the amount of time they choose to use the present device.

Figure 2:
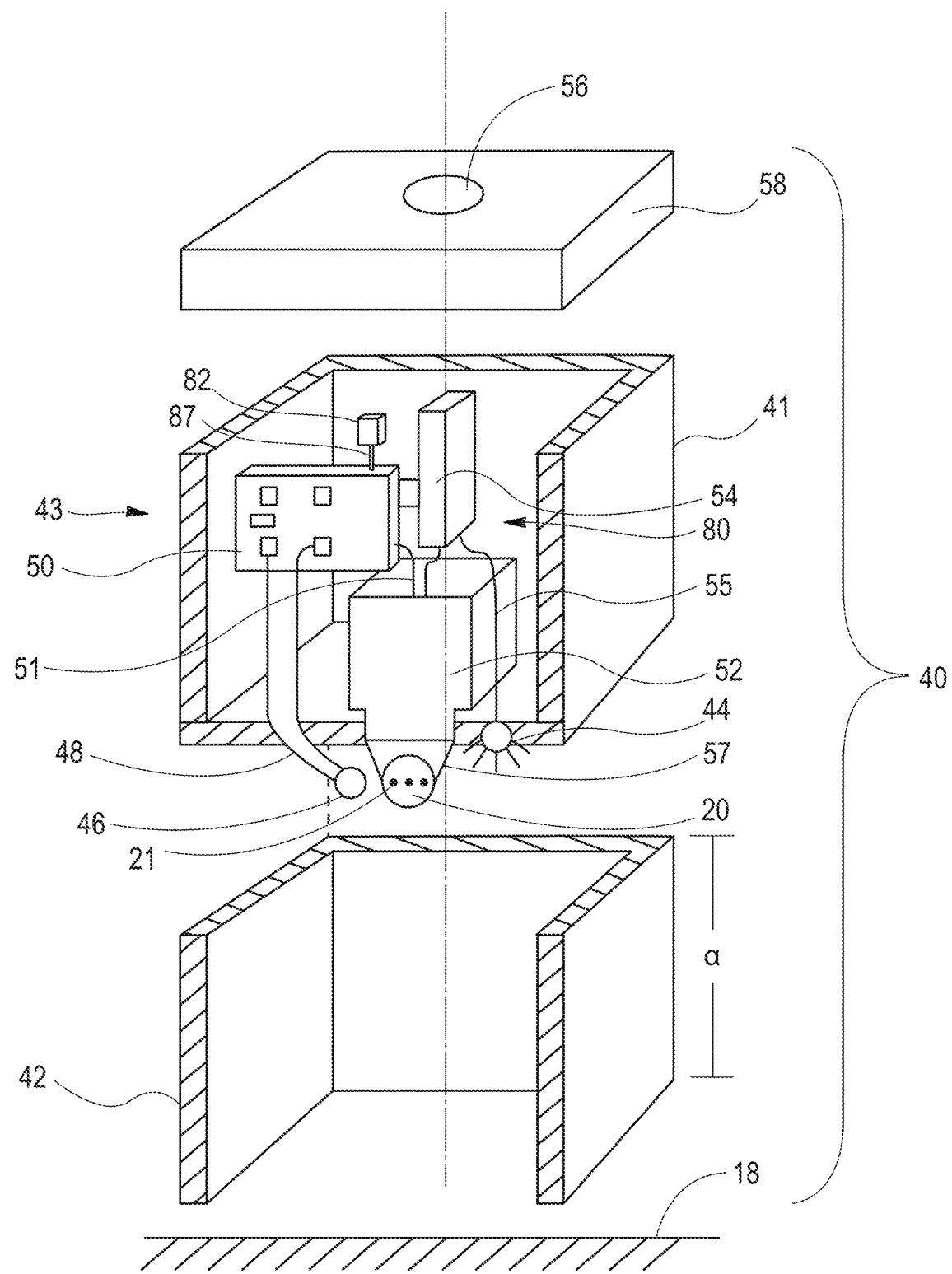
FIG. 2 is an exploded view of a personal care device according to the present invention.

FIG. 2 shows personal care device 40 comprising device cover 58, body 43, and physical spacer 42. Physical spacer 42 of personal care device 40 is directly above keratinous surface 18. Physical spacer 42 has a set, predetermined height a such that when it contacts keratinous surface 18, body 43 is at a known distance above keratinous surface 18. In one aspect, the height a is from about 1 mm to about 20 mm, alternatively from about 3 mm to about 15 mm, alternatively from about 4 mm to about 10 mm.

Body 43 can comprise the electrical and mechanical elements associated with personal care device 40, which can include light 44, sensor 46, image capture line 48, treatment element 80, processor 50, feedback element 82, signal line 87, cartridge line 51, power element 54, and one or more power lines 55.

In one embodiment, treatment element 80 can comprise nozzle array 20, cartridge die 57, and cartridge 52. Nozzle array 20 can comprise one or more nozzles 21 and can be embedded on cartridge die 57 which is attached to cartridge 52. Body 43 can be enclosed within device housing 41. Nozzle array 20 can be in a linear configuration, multiple rows, off-set, sine wave, curved, circular, saw tooth arrangements, and combinations thereof. Cartridge die 57 can be made of silicon, glass, machinable glass ceramic, sapphire, alumina, printed wiring board substrates (for example, glass-reinforced epoxy laminate material like FR4, Liquid Crystal Polymer, polyimide etc.) within which the nozzle array 20 can be formed.

Light 44 can illuminate the area of keratinous surface 18 within spacer 42 such that sensor 46 has relatively constant illumination. Background lighting can affect sensor 46 as portions of physical spacer 42 lift off keratinous surface 18 and allow background light in and the illumination from light 44 to escape. Small deviations in illumination can be corrected for provided light 44 provides a relatively constant background illumination. Light 44 can be a LED, incandescent light, neon bulb based, or any other commercially available source of illumination. Light 44 can have constant illumination or adjustable illumination. For example, an adjustable light source might be useful if the background illumination is excessively bright or dark.

Sensor 46 can be any component that is capable of obtaining a visual property of an area of keratinous surface, non-limiting examples of which can include optical sensors, image capture devices, spectrophotometers, photonic measuring devices for wavelengths within the visible spectrum as well as those wavelengths above and below the visible spectrum which could measure sub-surface features, and combinations thereof.

In one aspect, sensor 46 can be an image capture device that is capable of taking images of keratinous surface 18. The image capture device can be any of a variety of commercially available devices such as a simple camera or a digital cmos camera chip. In one aspect, sensor 46 can take a measurement of the L value of keratinous surface 18 and/or an image of keratinous surface 18 and can send it to processor 50 via image capture line 48 for analysis. In one aspect, the image may be analyzed for local L values, background L values, or both. Grey scale conversion occurs within the analytical processing capabilities of processor 50. The comparison of background L to local L to determine the $\Delta L_M$ occurs within processor 50, which can be a commercially available programmable chip, or other commercially available processing units.

Processor 50 is generally referred to as a central processing unit ("CPU"). The CPU can be a single programmable chip like those found in consumer electronic devices such as a laptop computer, a cell phone, an electric razor, and the like. The CPU may comprise an Application Specific Integrated Circuit (ASIC), controller, Field Programmable Gate Array (FPGA), integrated circuit, microcontroller, microprocessor, processor, and the like. The CPU may also comprise memory functionality, either internal to the CPU as cache memory, for example Random Access Memory (RAM), Static Random Access Memory (SRAM), and the like, or external to the CPU, for example as Dynamic Random-Access Memory (DRAM), Read Only Memory (ROM), Static RAM, Flash Memory (e.g., Compact Flash or SmartMedia cards), disk drives, Solid State Disk Drives (SSD), or Internet Cloud storage. While it is anticipated that a remote CPU, either tethered to the personal care device or which communicates wirelessly, can be used, a local CPU within the personal care device is exemplified herein.

Images can be taken in sequence or preferably continuously. An image capture device that takes a minimum of 4 frames per second is preferred. Higher speed image capture devices (greater than 4 frames per second) are desired as well, for example greater 100 frames per second, alternatively greater than 200 frames per second, alternatively greater than 600 frames per second. All images can be taken in a grey scale or converted to a grey scale, and the grey scale can have any range, for example, 0-255, no units. This corresponds approximately to a refresh rate of 0.2 seconds or faster. Consistent with the image capture device, the CPU can process at a rate of 100 frames per second, alternatively greater than 200 frames per second, alternatively greater than 600 frames per second.

The results of the image analysis, when compared to criteria pre-programmed into processor 50, may result in a desired modification of keratinous surface 18. In such a case, for example when the calculated $\Delta L_M$ exceeds the predetermined $\Delta L_S$, a signal is sent from processor 50 to cartridge 52, via cartridge line 51, to fire one or more nozzles 21 in nozzle array 20 and dispense a personal care composition. In one aspect, when processor 50 sends a signal to fire the one or more nozzles 21 in nozzle array 20, processor 50 can also send a signal to feedback element 82 to activate feedback element 82 to emit a feedback signal. In one aspect, the feedback signal is correlated to the rate of deposition of the personal care composition.

Feedback element 82 can comprise a speaker, a bell, chime, a piezo buzzer, a mechanical vibrating element, percussion element, a harmonic element, a mechanical deformation element, a light such as an LED, incandescent light, neon bulb, or any other commercially available light source, and combinations thereof.

In one aspect, every time processor 50 sends a signal to fire one or more nozzles 21, processor 50 can send a signal to activate feedback element 82. Alternatively, processor 50 can intermittently send a signal to activate feedback element 82 such that it is not activated every time one or more nozzles 21 is fired. In one aspect, the feedback element need not be activated and emit a feedback signal every time a droplet of the personal care composition is deposited. When a high number of droplets are deposited, the user may not be able to tell the variability in the feedback signal if there is a feedback signal for every droplet deposited.

In one aspect, intermittently activated can mean that the feedback element emits a feedback signal for every about 50 to about 500 droplets of personal care composition that are deposited, alternatively for every about 150 to about 400 droplets, alternatively for every about 200 to about 300 droplets. In one aspect, the feedback element can be activated and emit a feedback signal for every about 160 droplets of personal care composition that is deposited.

Alternatively, intermittently activated can mean that the feedback element emits a feedback signal for every about 0.005 μl to about 0.05 μl of personal care composition deposited, alternatively for every about 0.01 μl to about 0.03 μl.

In one aspect, the feedback element is activated when at least a portion of the personal care composition is being deposited. At least a portion of the personal care composition can mean that the feedback signal is emitted when a certain volume or number of personal care composition droplets are deposited. The volume or number of personal care composition droplets deposited for every feedback signal emitted can be any amount so long as the feedback signal is emitted in a manner that alerts the user to the rate of deposition.

In one aspect, the feedback signal can comprise an auditory signal, a visual signal, a vibratory signal, and combinations thereof. In one aspect, the auditory signal can be a sound. The sound can be a discontinuous sound such as a beep or click and the frequency, or cadence, of the sound can increase as the rate of deposition increases and the frequency can decrease as the rate of deposition decreases. Alternatively, the feedback signal can be continuous and the loudness (the decibels) of the feedback signal can increase as the rate of deposition increases. When the feedback signal is an auditory signal, the auditory signal can also change pitch, and the higher or lower the pitch, the higher or lower the rate of deposition. Alternatively, the feedback signal can be a visual signal such as a light, and the intensity (brightness) of the light can increase as the rate of deposition increases. Alternatively, the light can pulse and the frequency of the pulse can increase as the rate of deposition increases. The light can be any color that is visible on the skin. In one aspect, the feedback signal can be a vibration and the intensity of the vibration can increase as the rate of deposition increases and/or decrease as the rate of deposition decreases.

In one aspect, when the deposition flow rate is zero, feedback element 82 will not be activated or will be activated but will not emit a feedback signal. When processor 50 sends a signal to treatment element 82 to deposit the personal care composition, feedback element 82 can be activated to emit a feedback signal. In one aspect, the flow rate of the personal care composition can be correlated to the feedback signal. For example, when feedback element 82 is depositing a very low flow rate of the personal care composition, a low intensity feedback signal would be emitted, such as a low intensity vibration, low cadence click or beep, low volume sound, low intensity illumination, etc. Alternatively, when the device is depositing a high deposition flow rate, feedback element 82 would emit a high intensity vibration, high cadence click or beep, high volume sound, high intensity illumination, etc.

Power for cartridge 52, light 44, sensor 46, processor 50, feedback element 82, treatment element 80, and other mechanical and electrical elements that might be present can be supplied by power element 54 via one or more power lines 55. Power element 54 can be turned off and on, which in turn turns personal care device 40 off and on, via power switch 56 which can be located anywhere on personal care device 40, but is shown here on device cover 58. Power element 54 may include energy storage functionality via a battery, a rechargeable battery, an electrochemical capacitor, a double-layer capacitor, a supercapacitor, a hybrid battery-capacitor system, and combinations thereof.

Figure 3:
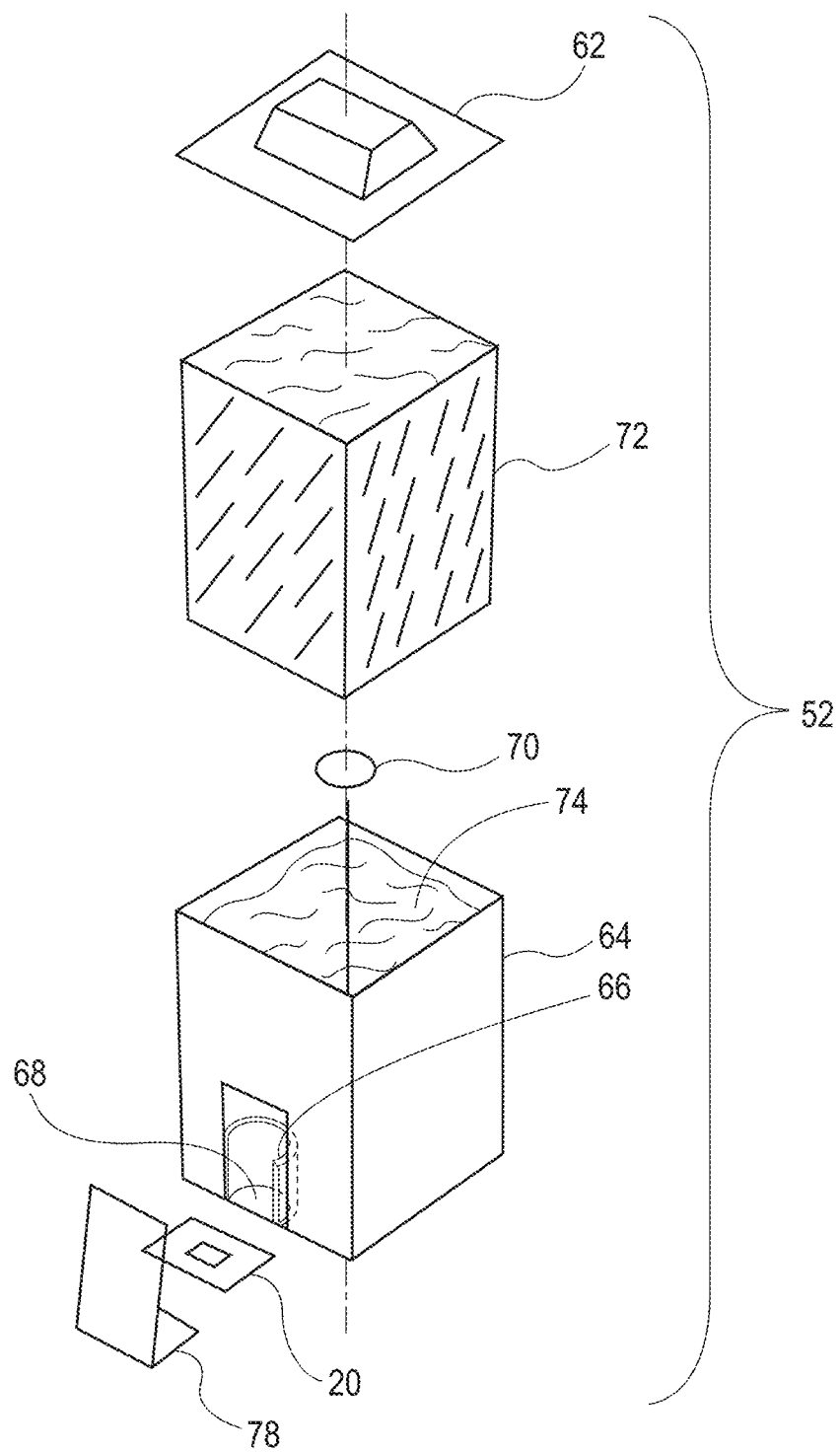
FIG. 3 is an exploded view of a cartridge according to the present invention.

Turning now to FIG. 3, which is an exploded view of the cartridge 52 comprising cartridge cap 62 and cartridge body 64. Cartridge body 64 includes standpipe 66 which is typically enclosed within cartridge body 64 and defines nozzle outlet 68. Optional filter 70 helps keep excessively large particles, and other debris out of the nozzle array 20. Filter 70 and nozzle array 20 are on opposite sides of nozzle outlet 68. Personal care composition 74 is contained within cartridge body 64. Foam core 72 at least partially fills cartridge 64 and helps to regulate back pressure of personal care composition 74. Back pressure can be regulated via bladders (not shown) and other methods known to the art. Foam core 72 shown here is just one example of how to help regulate the flow of the personal care composition 74 to standpipe 66 through filter 70 and into nozzle array 20. Connector 78 provides the electrical power and signal to nozzle array 20. Personal care composition 74 may be ejected from the cartridge 52 by piezoelectric means, thermal means, mechanical pumping means, or a combination of these.

Figure 4:
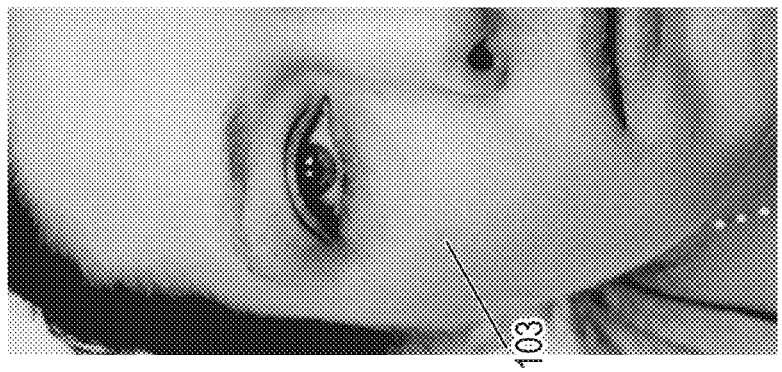
FIG. 4 is the natural, uncovered skin of a female user.
Figure 5:
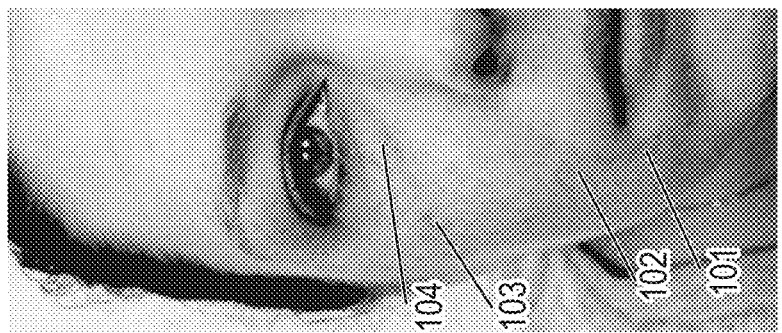
FIG. 5 is the same female user in FIG. 4 with applied makeup.
Figure 6:
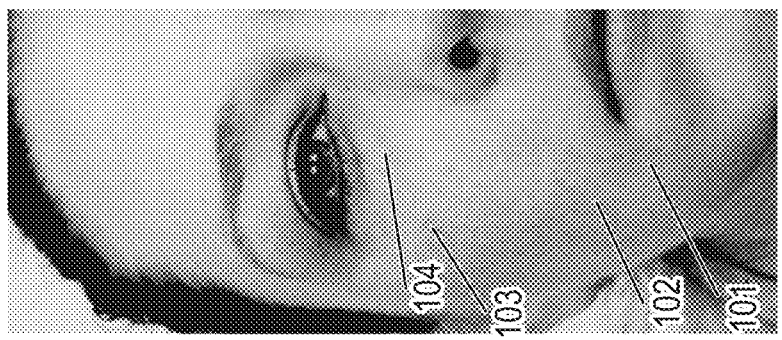
FIG. 6 is the same female user as shown in FIG. 4, with no makeup on, after using the personal care device of the present invention.

Referring now to FIGS. 4, 5, and 6, which are photographs of the same female subject. FIG. 4 represents the subject's washed, natural, and uncoated skin. FIG. 5 was taken after the subject applied makeup to her face in a manner she would normally do. FIG. 6 was taken after the subject's makeup was removed and her face treated with the personal care device described herein. FIGS. 4, 5, and 6 are all taken on the same day, with no appreciable sun exposure between photographs (i.e. the subject was indoors for the entire modification period).

Keratinous imperfections 101, 102, 103 and 104 are clear in FIG. 4. After makeup is applied, keratinous imperfections 101, 102, 103 and 104 are all still visible as shown in FIG. 5. FIGS. 4 and 5 show that makeup changes the overall tone of human skin, but does not cover up the keratinous imperfections.

The subject washed her face to remove the applied makeup after the photograph of FIG. 5 was taken. The subject's skin was then modified with the personal care device and the photograph of FIG. 6 was taken. Keratinous imperfections 101, 102 and 104 from FIGS. 4 and 5 are largely invisible in FIG. 6. Keratinous imperfection 103 is barely visible after modification with the personal care device. The personal care device provides a substantial and visible change to the appearance of human skin versus the natural condition of the skin and the skin with applied makeup.

While the personal care device described above is one embodiment, other embodiments are envisioned in which the personal care device can comprise a treatment element adapted to deliver energy, such as by a laser, to the keratinous surface. In this case, the feedback signal can be correlated to the intensity of energy rather than rate of deposition that the personal care device is delivering to the keratinous surface.

The background L can be calculated anywhere within the image. The image is taken where the nozzles will fire the personal care composition. The background L can be the arithmetic average, median, or mean of a plurality of local $L_S$, which means the calculation can include all of the local $L_S$ in the image, or a subset thereof.

The predetermined $\Delta L_S$ is the absolute value of the difference between the local L and the background L. This value, $\Delta L_S$, can be defined in absolute numbers or as a percentage. The sensor is for example a camera that takes black and white or color images, a spectrophotometer, or similar devices that are sensitive to electromagnetic energy wavelengths. The images are taken, or converted to a standard grey scale that is known to the art. It is understood that any numerical scale that measures lightness to darkness can be considered a "grey scale". Moreover, as used herein, "grey scale" is intended to be a linear scale, or one band, or one visual attribute. For example, one "grey scale" visual attribute could be single wavelength or a narrow wavelength to define a specific visual color. Another example of one "grey scale" visual attribute could be a mix of wavelength numerical values averaged for each pixel making up the image, such as a true black, grey or white image from a RGB mixture.

It will also be understood by those skilled in the art that the background L value should not be too close to the ends of this scale. For example, if the grey scale is 0-100, with 0 being pure black and 100 being pure white, a background in the 0-10 range, or in the 90-100 range may be too light or too dark to show meaningful differences. Accordingly, one can adjust the background lighting, or the gain on the sensor taking the image, to move the background L closer to the middle of the scale. In this example, a background L of 50 would be ideal, with a background L in the range of 10-90 preferred, 20-80 even more preferred.

The most common grey scale is 0-255 (no units) and other examples include 0-1024 and 0-4096. For a grey scale of 0-255, the difference between grey scale steps is at least 1/255. In this example, it would be desirable to use sensor and lighting settings that provide a background L value between 60 and 210. Using the 0-255 gray scale, the $\Delta L_S$ is preferably at least 0.5, more preferably at least 1, and even more preferably at least 1.5, to initiate modification of the keratinous surface. Likewise, $\Delta L_S$ can be measured as a percentage, for example, a numerical $\Delta L_S$ of 2.6 is approximately equal to 1.0% of a 255 grey scale. Thus, $\Delta L_S$ may be plus or minus 0.25%, preferably plus or minus 0.5%, even more preferably plus or minus 0.75%, of the grayscale.

There is no technical difference between an image used for background L values and those used for local L values, the difference is in the analysis of the image. Hence, the images are continually sent to the processor to calculate the L values and $\Delta L_M$ values. By "sent" it is understood, that preferably at least 4 bits of data per pixel are transferred for each image, and preferably, this 4 bit (or more) packet of data is used in the calculation of each local L value. It is understood, that the background L can be calculated once in a modification period and that value can be reused throughout the modification period. Alternatively, it can be continually recalculated as long as the modification process goes on. Moreover, there can be pre-programmed triggers to initiate a recalculation of the background L. Also, the background L may be retrieved from the processor memory to be used for the current background L. For example, if an extended period of time elapses and no keratinous imperfections are found, or if keratinous imperfections are being found too frequently, a new background L might automatically be calculated. Likewise, $\Delta L_S$ can be a set value that remains constant throughout the modification process or it too can vary. $\Delta L_S$ can be reset during the modification process for any of a variety of reasons. If too many nozzles are firing too frequently, the $\Delta L_S$ can be adjusted to lower the intensity of the nozzle firing. Similarly, if the nozzles are firing too infrequently, $\Delta L_S$ can be adjusted in the opposite direction to increase the sensitivity of keratinous imperfection detection. Those skilled in the art will appreciate that modifying $\Delta L_S$ during the modification process is a matter of programming the processor to or with a desired algorithm.

When the $\Delta L_M$ exceeds the predetermined value, the keratinous imperfection is modified with the personal care composition. Modification requires firing one or more of the nozzles which dispense the personal care composition onto the keratinous surface in the area of the keratinous imperfection.

More specifically, the personal care composition is deposited via an array of nozzles and the local L is calculated along the length of, and in the firing range of, the array of nozzles. The "firing range" of a nozzle will vary based on its size, type, the speed the device is moving, distance from the target, and other parameters. Examples of various types of nozzles suitable for use in the present devices are given below. In general, "near the nozzle" as used herein is intended to mean the image taken to calculate a local L value is close to the area of keratinous surface where the personal care composition is deposited by the nozzle (the firing range, or landing zone of the nozzle). Without intending to limit the invention, near the nozzle means the image should be taken within a radius of about 2 cm, preferably about 1 cm, and even more preferably about 0.7 cm from the center of the nozzle.

An individual nozzle may be fired to deposit the personal care composition, or multiple nozzles can be fired at the same time. The number of nozzles fired along the array of nozzles can be adjusted based on the size of the $\Delta L_M$ and the size of the keratinous imperfection. Furthermore, the frequency of nozzle firing can be adjusted based on the $\Delta L_M$, with more droplets being fired in succession in response to larger $\Delta L_M$ values.

Firing intensity curves can be programmed into the processor to adjust the firing rate of nozzles. For example, if $\Delta L_M$ is equal to or slightly greater than $\Delta L_S$, then the adjacent nozzle is fired 1 time. If $\Delta L_M$ increases to $2 * \Delta L_S$, then the adjacent nozzle is fired 25 times. If the $\Delta L_M$ is $3 * \Delta L_S$, then the adjacent nozzle is fired 100 times. This non-limiting example is intended to show how the size of the $\Delta L_M$ with respect to the $\Delta L_S$ can determine the amount, and hence, the intensity of the firing of the nozzles adjacent the keratinous imperfection. Those skilled in the art will appreciate that plotting a firing intensity curve using 2, 3, or more data points, and then programming that firing intensity curve into the processor are known techniques.

While inkjet cartridges are shown and exemplified herein, personal care compositions may be applied with other "flow control" devices. Flow control devices typically are characterized as "drop control techniques" where individual droplets of the substance are controlled. Ink jet printers, which are known to the art, are examples of drop on demand applicators and this technology is applicable for use in the present invention. Piezo electric drop control devices and other micro electromechanical systems are appropriate for use with the current personal care device. Spray devices and electrostatic spray devices are non-drop control techniques where droplets are produced and controlled only in aggregate. Often in a spray device, a lack of individual droplet control, or "randomness" is desired in order to produce a smooth application over a relatively large area. By contrast, it can be desirable to provide very specific control of the amount and placement of the personal care compositions.

Examples of drop control can include "fine flow control" where the flow of the substance is precisely controlled to deliver droplets as desired and "inkjet technologies." An older inkjet technology includes supplying a continuous flow of charged droplets past electrostatic deflector plates which are alternately charged so that the plates either permit a droplet to pass or deflect to a gutter. Other inkjet technologies include "drop on demand" such as thermal devices provided by Hewlett-Packard, and piezoelectric devices such as provided by Epson® and other printer manufacturers. In one embodiment of the current invention, a drop on demand technology is combined with charging the droplets.

In one aspect, the personal care device can deposit a personal care composition via inkjet deposition, however, other methods of deposition can include direct contact, atomized spray deposition, and combinations thereof.

The personal care device of the present invention is preferably handheld but can be tethered to a structure that moves the personal care device across the keratinous surface to be modified. If handheld, the user can simply move the personal care device across the keratinous surface to be modified. Optionally, multiple personal care devices can be configured in a stationary structure wherein the user places the keratinous surface to be modified and multiple readings and applications occur simultaneously or in sequence.

The personal care composition can be applied to the keratinous surface by scanning and applying at the same time while making multiple passes over the surface. Several advantages result from using multiple pass application. The process for multiple pass applications is to make a partial application of the personal care composition, then to scan again the area of keratinous surface that has received the partial application. A further application of personal care compositions can be made, and still further multiple pass scanning and applications can be made to approach an aesthetic goal. Thus, the user can select the end point of the modification, i.e. the "aesthetic goal", thus tailoring the modification time to individual needs and preferences. Attempting to make all corrections in one pass has been shown to overcorrect in certain areas.

It may be desirable for the personal care device to modify from about 1% to about 40% of the keratinous surface with a personal care composition, alternatively less than about 20%, alternatively less than about 10%, alternatively less than about 5%, alternatively less than about 1%, alternatively less than about 0.5%. This can be desirable because it can provide a reduced tactile impact as more of the user's basal skin is exposed and not covered by the pigmented cosmetic composition.

The personal care device may apply the personal care composition in droplets having an average diameter of from about from about 0.1 µm to about 50 µm. Preferably, the personal care composition can be applied to the keratinous imperfection in a discontinuous pattern of discrete droplets.

In one aspect, the volume of personal care composition droplet deposited by the personal care device is about 100 picoliters.

In one aspect, the feedback signal can help with habit formation and compliance with proper usage techniques.

In one aspect, the feedback element can be activated when the personal care device is placed against the keratinous surface with the proper amount of pressure. In this case, the feedback element can emit a second feedback signal to alert the user that the correct amount of pressure is being applied. In one aspect, the second feedback signal can be correlated to the amount of pressure applied to the keratinous surface.

In another aspect, the personal care device can comprise a plurality of rollers on the proximal end of the physical spacer and can help the personal care device move across the keratinous surface. In one aspect, the feedback element can be activated and can emit a third feedback signal when any one of the plurality of rollers lifts off of the keratinous surface.

In another aspect, the feedback element may emit a fourth feedback signal when the personal care device is being used improperly to inform the user the personal care device is not working properly. For example, when the sensor is unable to properly sense a keratinous surface due to the distance from the surface and/or the angle of the sensor to the surface or when the personal care composition is depleted or nearly depleted.

In another aspect, the feedback element may stop emitting a feedback signal when the personal care device is being moved across the keratinous surface too quickly. In one aspect, the camera can be used to determine the approximate speed at which the personal care device is moved across the keratinous surface ("modification speed") by analyzing moving elements of the image being captured. In one aspect, there can be rollers that are in contact with the keratinous surface that are in the camera's field of view. The rotational rate of the rollers can be calibrated to a linear surface travel speed and when the rotational rate exceeds the desired modification speed, the auditory signal can be turned off. Alternatively, the camera's resolution can be correlated to the spatial size of surface image elements. In this case, surface features can be monitored for how quickly they pass through the camera's field of view and this rate of image movement can be used to approximate the modification speed. In one aspect, when the modification speed is greater than about 1.5 inches per second the nozzles may not fire and no feedback signal is emitted. It is believed that when the feedback signal is no longer emitted, it can signal the user to decrease the modification speed, resulting in better deposition quality and modification of keratinous imperfections. Alternatively, the feedback element may emit a fifth feedback signal when the modification speed is greater than about 1.5 inches per second.

Personal Care Composition

The personal care composition can hide or camouflage a keratinous imperfection, such as hyperpigmentation, when deposited precisely and substantially only onto the keratinous imperfection.

One important characteristic of the personal care compositions of the present invention is the contrast ratio. The contrast ratio of the personal care composition when depositing it onto a keratinous surface like skin is at least 0.1. The contrast ratio is preferably between about 0.1 and about 1.0, more preferably between about 0.2 and about 1.0, and most preferably between about 0.3 and about 1.0. As used herein, "contrast ratio" refers to the opacity of the personal care composition, or the ability of the personal care composition to reduce or prevent light transmission, determined after the composition is drawn onto an opacity chart (Form N2A, Leneta Company of Manwah, N.J., or the equivalent thereof) and by using a spectrophotometer with settings selected to exclude specular reflection. To measure the contrast ratio, the personal care composition is diluted with 1% Stabylen 30 in a deionized water premix at a 10:1 ratio. It is applied to the top of the opacity chart and then is drawn into a film having a thickness of approximately 0.01 inches using a film applicator (e.g., as commercially available from BYK Gardner of Columbia, Md., or the equivalent thereof). The film is allowed to dry for 2 hours under conditions of 22° C.+/−1° C., 1 atm. Using a spectrophotometer, the Y tristimulus value (i.e., the XYZ color space) of the film is measured and recorded. The Y tristimulus value is measured in three different areas of the film over the black section of the opacity chart, and also in three different areas of the film over the white section of the opacity chart.

The keratinous surface lightness and personal care composition lightness can be measured by a calibrated spectrophotometer using known methods. In one example, when using a calibrated spectrophotometer, the average L value of human skin usually spans the range of about 25 to 75. In this case, the corresponding personal care composition has a lightness value of at least 2 units greater, preferably at least 3 units greater, and even more preferably at least 5 units greater than the average skin lightness value of the user.

The personal care composition can comprise particles. In one aspect, personal care composition preferably comprises a particle settling rate of less than 0.06 mm per day at 25° C. and 1 atm pressure. Particle settling can be measured according to ASTM Method D869-85 (Jun. 1, 2015). The personal care composition may further have an elastic (or Young's) modulus between about 0.1 Pa to about 1000 Pa at 25° C. and 1000 Hz. Elastic modulus can be measured according to ASTM Method E111-17 (Jul. 15, 2017). Solid wax based personal care compositions may have an elastic modulus of up to about 100 MPa. Preferably, the particles in the personal care composition have a refractive index of between about 1.1 and about 5.0.

The personal care composition can comprise inks, dyes, pigments, adhesives, curable compositions, optically activated compounds, metal oxides such as iron, zinc, titanium oxides, and mixtures thereof, bleaching agents, texture reducing polymers, cosmetics, hair colorants, and combinations thereof. In one aspect, the personal care composition can comprise metal oxides comprising an average particle size of greater than about 100 nm.

In one aspect, the personal care composition can be a skin care composition, a hair care composition, a hair removal composition (often referred to as depilatories), a hair growth stimulant, and mixtures thereof.

The personal care compositions can be delivered alone or in the presence of a dermatologically-acceptable carrier. The phrase "dermatologically-acceptable carrier", as used herein, means that the carrier is suitable for topical application to the keratinous tissue, has good aesthetic properties, is compatible with any additional components of the personal care composition, and will not cause any untoward safety or toxicity concerns. The carrier can be in a wide variety of forms. Non-limiting examples include simple solutions (water or oil based) and emulsions. In certain embodiments, the dermatologically acceptable carrier is in the form of an emulsion. Emulsions may be generally classified as having a continuous aqueous phase (e.g., oil-in-water and water-in-oil-in-water) or a continuous oil phase (e.g., water-in-oil and oil-in-water-in-oil). The oil phase may comprise silicone oils; non-silicone oils such as hydrocarbon oils, esters, ethers, and the like; and mixtures thereof. Emulsion carriers can include, but are not limited to, continuous water phase emulsions such as silicone-in-water, oil-in-water, and water-in-oil-in-water emulsions; continuous oil phase emulsions such as water-in-oil and water-in-silicone emulsions; oil-in-water-in-silicone emulsions; and combinations thereof.

In one aspect, the personal care composition can be oil-free.

The personal care composition can be delivered in a variety of product forms including, but not limited to, a cream, a lotion, a gel, a foam, a paste, or a serum.

The personal care composition can optionally include for purposes of proper formulation and stabilization anti-fungal and anti-bacterial components.

The personal care composition can comprise a humectant as a carrier or chassis for the other components in the personal care composition. An exemplary class of humectants can include polyhydric alcohols. Suitable polyhydric alcohols include polyalkylene glycols and alkylene polyols and their derivatives, including propylene glycol, dipropylene glycol, polypropylene glycol, polyethylene glycol and derivatives thereof; sorbitol; hydroxypropyl sorbitol; erythritol; threitol; pentaerythritol; xylitol; glucitol; mannitol; butylene glycol (e.g., 1,3-butylene glycol); pentylene glycol; hexane triol (e.g., 1,2,6-hexanetriol); glycerin; ethoxylated glycerine; and propoxylated glycerine. Other suitable humectants can include sodium 2-pyrrolidone-5-carboxylate; guanidine; glycolic acid and glycolate salts (e.g., ammonium and quaternary alkyl ammonium); lactic acid and lactate salts (e.g., ammonium and quaternary alkyl ammonium); aloe vera in any of its variety of forms (e.g., aloe vera gel); hyaluronic acid and derivatives thereof (e.g., salt derivatives such as sodium hyaluronate); lactamide monoethanolamine; acetamide monoethanolamine; urea; sodium pyroglutamate, water-soluble glyceryl poly(meth) acrylate lubricants (such as Hispagel®); and mixtures thereof.

Inks, dyes, metal oxides and pigments (collectively referred to as "colorants" below) can be used to modify the color or reflectance of the keratinous surface. Compositions comprising colorants are commonly used to modify color and reflectance in cosmetic make-up compositions. Foundation, lipstick, eyeliner are just a few examples of these make-up compositions, but they are all applied evenly across large portions of the keratinous surface, that is they are macro-applications. In sharp contrast, the present personal care compositions are selectively applied on a very small scale to select areas, that is they are intended for a micro-application.

Suitable colorants may include inorganic or organic pigments and powders. Organic pigments can include natural colorants and synthetic monomeric and polymeric colorants. Organic pigments include various aromatic types such as azo, indigoid, triphenylmethane, anthraquinone, and xanthine dyes which are designated as D&C and FD&C blues, browns, greens, oranges, reds, yellows, etc. Organic pigments may consist of insoluble metallic salts of certified color additives, referred to as the Lakes. Inorganic pigments include iron oxides, ferric ammonium ferrocyanide, manganese violet, ultramarines, chromium, chromium hydroxide colors, and mixtures thereof. The pigments may be coated with one or more ingredients that cause the pigments to be hydrophobic. Suitable coating materials that will render the pigments more lipophilic in nature include silicones, lecithin, amino acids, phospholipids, inorganic and organic oils, polyethylene, and other polymeric materials. Suitable silicone treated pigments are disclosed in U.S. Pat. No. 5,143,722. Inorganic white or uncolored pigments include $TiO_2$, ZnO, or ZrO$_2$, which are commercially available from a number of sources. Other suitable colorants are identified in U.S. Pat. No. 7,166,279. Colorants are generally included at a weight percent such that the personal care composition yields a perceptible color. In one aspect, the personal care composition exhibits a color that is perceptibly different from the color of the applicator. Perceptibly different refers to a difference in color that is perceptible to a person having normal sensory abilities under standard lighting conditions (e.g., natural illumination as experienced outdoors during daylight hours, the illumination of a standard 100 watt incandescent white light bulb at a distance of 2 meters, or as defined by CIE D65 standard illuminate lighting at 800 lux to a 1964 CIE standard observer).

In one aspect, the personal care composition can comprise greater than about 15 wt % colorant, alternatively greater than about 20 wt %, alternatively greater than about 30 wt %. In one aspect, the personal care composition can comprise from about 1 to about 30 wt % colorant, alternatively from about 3 to about 25 wt %, alternatively from about 5 to about 20 wt %, alternatively from about 8 to about 18 wt %.

The personal care composition can comprise an adhesive that is compatible with keratinous surfaces. Commercially available adhesives compatible with keratinous surfaces are available from the 3M Corporation (Minneapolis, Minn.). See, for example: U.S. Pat. No. 6,461,467, issued to Blatchford, et al.; U.S. Pat. No. 5,614,310, issued to Delgado, et al.; and U.S. Pat. No. 5,160,315, issued to Heinecke et al. In one aspect, a personal care composition comprising an adhesive can be selectively applied to the keratinous surface and a second personal care composition can be dusted on the keratinous surface where can will stick to the adhesive. The second personal care composition that is not adhered to the keratinous surface can then be removed leaving behind a selective, micro application of the second personal care composition.

Likewise, the personal care composition can comprise curable compositions that cure upon exposure to certain wavelengths of energy, infrared light for example. In one aspect, a personal care composition comprising a curable composition can be selectively applied to the keratinous surface and can be cured by exposing the keratinous surface to the curing energy source. The entire keratinous surface can be exposed, or the exposure can be done at the same time as the application.

The personal care composition can be an anti-wrinkle composition comprising a tensioning polymer and/or film-forming polymers. Suitable tensioning polymers are described in US Patent Applications US20060210513A1, filed by Luizzi, et al. and suitable film-forming polymers are described in US20070148120A1, filed by Omura et al.

The personal care composition can comprise optically-activated particles. Sometimes referred to as "interference pigments", these optically-activated particles include a plurality of substrate particles selected from the group consisting of nylons, acrylics, polyesters, other plastic polymers, natural materials, regenerated cellulose, metals, minerals, and combinations thereof; an optical brightener chemically bonded to each of the plurality of substrate particles to form integral units in the form of optically-activated particles for diffusing light. These particles can help to reduce the visual perception of skin imperfections, including cellulite, shadows, skin discolorations, and wrinkles. Each of the optically-activated particles can be encapsulated with an ultra-violet (UV) transparent coating to increase the diffusion light to further reduce the visual perception of the keratinous imperfections. The encapsulated optically-activated particles can absorb UV radiation and emit visible light. The encapsulated optically-activated particles can both scatter and absorb light in a diffuse manner in order to reduce the visual perception of keratinous imperfections when the optically-activated particles are applied to the keratinous surface.

The personal care composition can be a skin care composition such as a moisturizer, a conditioner, an anti-aging composition, a skin lightening composition, a sunscreen, a sunless tanner, and combinations thereof.

The personal care composition may comprise a safe and effective amount of one or more actives useful for regulating and/or improving skin condition. "Safe and effective amount" means an amount of a compound or composition sufficient to induce a positive benefit but low enough to avoid serious side effects (i.e., provides a reasonable benefit to risk ratio within the judgment of a skilled artisan). A safe and effective amount of an active can be from about $1 \times 10^{-6}$ to about 25% by weight of the total composition, alternatively from about 0.0001 to about 25% by weight of the total composition, alternatively from about 0.01 to about 10% by weight of the total composition, alternatively from about 0.1 to about 5% by weight of the total composition, alternatively from about 0.2 to about 2% by weight of the total composition.

Suitable actives include, but are not limited to, vitamins (e.g., B3 compounds such as niacinamide, niacinnicotinic acid, tocopheryl nicotinate; B5 compounds, such as panthenol; vitamin A compounds and natural and/or synthetic analogs of Vitamin A, including retinoids, retinol, retinyl acetate, retinyl palmitate, retinoic acid, retinaldehyde, retinyl propionate, carotenoids (pro-vitamin A); vitamin E compounds, or tocopherol, including tocopherol sorbate, tocopherol acetate; vitamin C compounds, including ascorbate, ascorbyl esters of fatty acids, and ascorbic acid derivatives such as magnesium ascorbyl phosphate and sodium ascorbyl phosphate, ascorbyl glucoside, and ascorbyl sorbate), peptides (e.g., peptides containing ten or fewer amino acids, their derivatives, isomers, and complexes with other species such as metal ions), sugar amines (e.g., N-acetyl-glucosamine), sunscreens, oil control agents, tanning actives, anti-acne actives, desquamation actives, anti-cellulite actives, chelating agents, skin lightening agents, flavonoids, protease inhibitors (e.g., hexamidine and derivatives), non-vitamin antioxidants and radical scavengers, salicylic acid, hair growth regulators, anti-wrinkle actives, anti-atrophy actives, minerals, phytosterols and/or plant hormones, tyrosinase inhibitors, N-acyl amino acid compounds, moisturizers, plant extracts, and derivatives of any of the aforementioned actives. The term "derivative" as used herein refers to structures which are not shown but which one skilled in the art would understand are variations of the basic compound. For example, removing a hydrogen atom from benzene and replacing it with a methyl group. Suitable actives are further described in U.S. Patent Application Nos. US2006/0275237A1 and US2004/0175347A1.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A personal care device for modifying a keratinous surface comprising
    a. a sensor; wherein the sensor is a camera
    b. a treatment element comprising one or more nozzles and a cartridge containing a personal care composition;
    c. a feedback element; and
    d. a processor;
        wherein the sensor is operatively associated with the processor;
        wherein the processor is operatively associated with the treatment element and the feedback element;
        wherein the feedback element is activated during deposition of the personal care composition;
        wherein the feedback element emits a feedback signal when activated and the feedback signal corresponds to the rate of deposition of the personal care composition.

2. The personal care device of claim 1 wherein the feedback signal is selected from an auditory signal, a vibratory signal, a visual signal, and combinations thereof.

3. The personal care device of claim 2 wherein the feedback signal is an auditory signal and the auditory signal comprises a sound property that varies based on the rate of deposition and wherein the sound property is selected from volume, pitch, tone, and combinations thereof.

4. The personal care device of claim 1 wherein the feedback element is activated and emits a feedback signal for every 0.005 µl to 0.05 µl of the personal care composition deposited.

5. The personal care device of claim 1 wherein the feedback element is activated and emits a feedback signal for every 50 to 500 droplets of the personal care composition deposited.

6. The personal care device of claim 1 wherein the personal care device is a thermal inkjet printer.

7. A method of modifying a keratinous surface comprising the steps of
    a. identifying an area of keratinous surface comprising a keratinous imperfection;
    b. providing the personal care device of claim 1;
    c. contacting the personal care device with the area of keratinous surface and moving the personal care device over the area of keratinous surface;
    d. taking an image of the keratinous surface adjacent to the one or more nozzles;
    e. identifying the keratinous imperfection;
    f. depositing the personal care composition onto the keratinous imperfection;
    g. intermittently providing a feedback signal to alert the user that the personal care composition is deposited.

8. The method of claim 7 wherein the personal care device is moved over the area of keratinous surface at a stroke rate of about 0.5 to about 1.5 inches per second.

9. The method of claim 7 wherein the personal care device is moved across the skin at a modification speed and wherein when the modification speed is greater than about 1.5 inches per second the feedback signal is not emitted.

10. The method of claim 7 wherein the personal care device is moved over the area of keratinous surface until a feedback signal is emitted at a rate of less than about 5 signals per inch.

11. The personal care device of claim 1 wherein the feedback element is intermittently activated during the personal care composition deposition.

12. The personal care device of claim 2 wherein the feedback signal intensity decreases as the rate of deposition decreases.

13. The personal care device of claim 1 wherein the processor intermittently activates the feedback element when the one or more nozzles deposit the personal care composition.

14. The personal care device of claim 1 wherein the camera is capable of taking images of the keratinous surface.

15. The personal care device of claim 14 wherein the processor analyzes the images of the keratinous surface to identify a keratinous imperfection.

* * * * *